(12) United States Patent
Koiso et al.

(10) Patent No.: US 11,103,125 B2
(45) Date of Patent: Aug. 31, 2021

(54) ENDOSCOPE SYSTEM AND CIRCUITRY THAT CORRECTS DISTORTION BASED ON IMAGE SIZE

(71) Applicant: Sony Olympus Medical Solutions Inc., Tokyo (JP)

(72) Inventors: Manabu Koiso, Kanagawa (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 562 days.

(21) Appl. No.: 16/034,541

(22) Filed: Jul. 13, 2018

(65) Prior Publication Data
US 2019/0053693 A1    Feb. 21, 2019

(30) Foreign Application Priority Data

Aug. 17, 2017    (JP) .............................. JP2017-157489

(51) Int. Cl.
*A61B 1/04*      (2006.01)
*A61B 1/045*      (2006.01)
(Continued)

(52) U.S. Cl.
CPC ...... *A61B 1/00105* (2013.01); *A61B 1/00006* (2013.01); *A61B 1/00009* (2013.01); *A61B 1/00013* (2013.01); *A61B 1/00045* (2013.01); *A61B 1/00059* (2013.01); *A61B 1/00188* (2013.01); *A61B 1/042* (2013.01); *G02B 23/2484* (2013.01); *G02B 27/0075* (2013.01); *H04N 5/2257* (2013.01); *A61B 1/00018* (2013.01); *A61B 1/00124* (2013.01); *A61B 1/045* (2013.01); *H04N 5/2256* (2013.01); *H04N 2005/2255* (2013.01)

(58) Field of Classification Search
None
See application file for complete search history.

(56) References Cited

U.S. PATENT DOCUMENTS 6,063,023 A *   5/2000   Sakiyama .......... A61B 1/00193
                                                           600/117
7,834,907 B2 *   11/2010   Kawai .................. H04N 5/2628
                                                           348/208.4

(Continued)

FOREIGN PATENT DOCUMENTS

| JP | 2005057605 A | 3/2005 |
|---|---|---|
| JP | 2015-134039 | 7/2015 |

*Primary Examiner* — Michael J Carey
*Assistant Examiner* — Minqiao Huang
(74) *Attorney, Agent, or Firm* — Xsensus LLP

(57) ABSTRACT

An endoscope system is disclosed that included a camera head, a detection unit, and a distortion correction processing unit. The camera head is detachably connected to an eyepiece unit of a plurality of types of endoscopes inserted into a subject, the camera head including an imaging unit that captures a subject image received from an endoscope among the plurality of types of endoscopes that is connected to the eyepiece. The detection unit that detects a size of the subject image in the captured image on the basis of a luminance signal of each pixel in the captured image obtained by the imaging unit. The distortion correction processing unit that corrects an optical distortion of the captured image depending on sizes of a plurality of different subject images.

10 Claims, 11 Drawing Sheets

(51) Int. Cl.
  *A61B 1/00*   (2006.01)
  *G02B 23/24*  (2006.01)
  *H04N 5/225*  (2006.01)
  *G02B 27/00*  (2006.01)

(56) References Cited

U.S. PATENT DOCUMENTS

| | | | |
|---|---|---|---|
| 8,556,803 B2* | 10/2013 | Shigeta | A61B 1/04 600/118 |
| 2010/0034428 A1* | 2/2010 | Fukunishi | G06T 7/223 382/107 |
| 2014/0185006 A1* | 7/2014 | Yonezawa | A61B 3/14 351/206 |
| 2014/0285676 A1* | 9/2014 | Barreto | H04N 17/002 348/187 |
| 2015/0238276 A1* | 8/2015 | Atarot | A61B 1/00004 600/424 |
| 2016/0100741 A1* | 4/2016 | Ono | H04N 5/2354 600/109 |

* cited by examiner

FIG.3
(a)
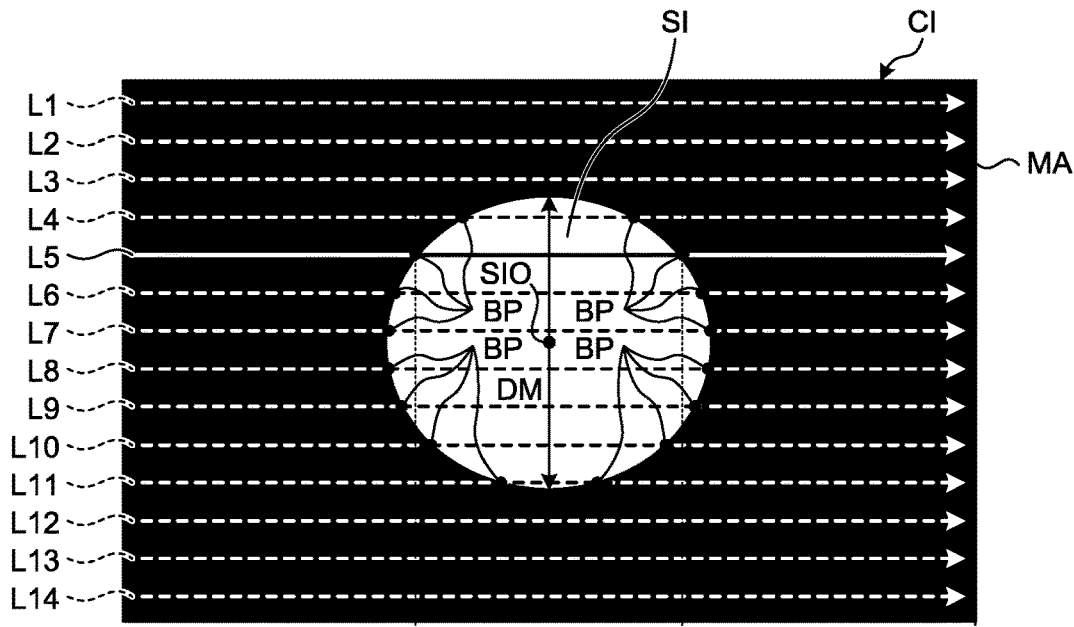
(b)
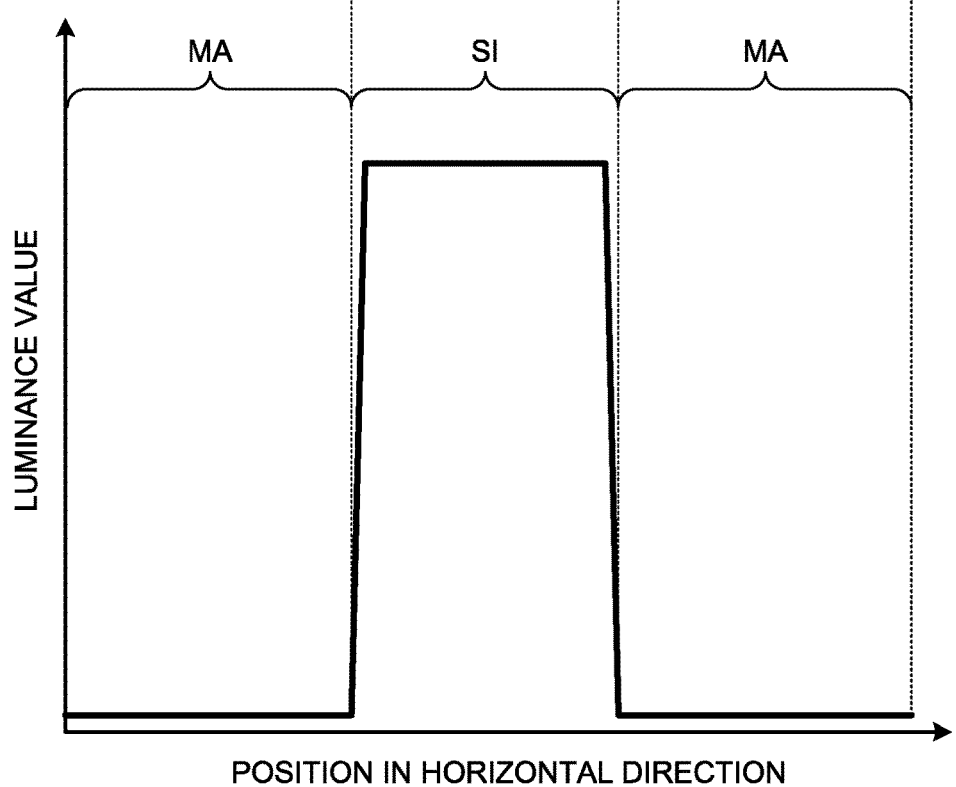

FIG.4
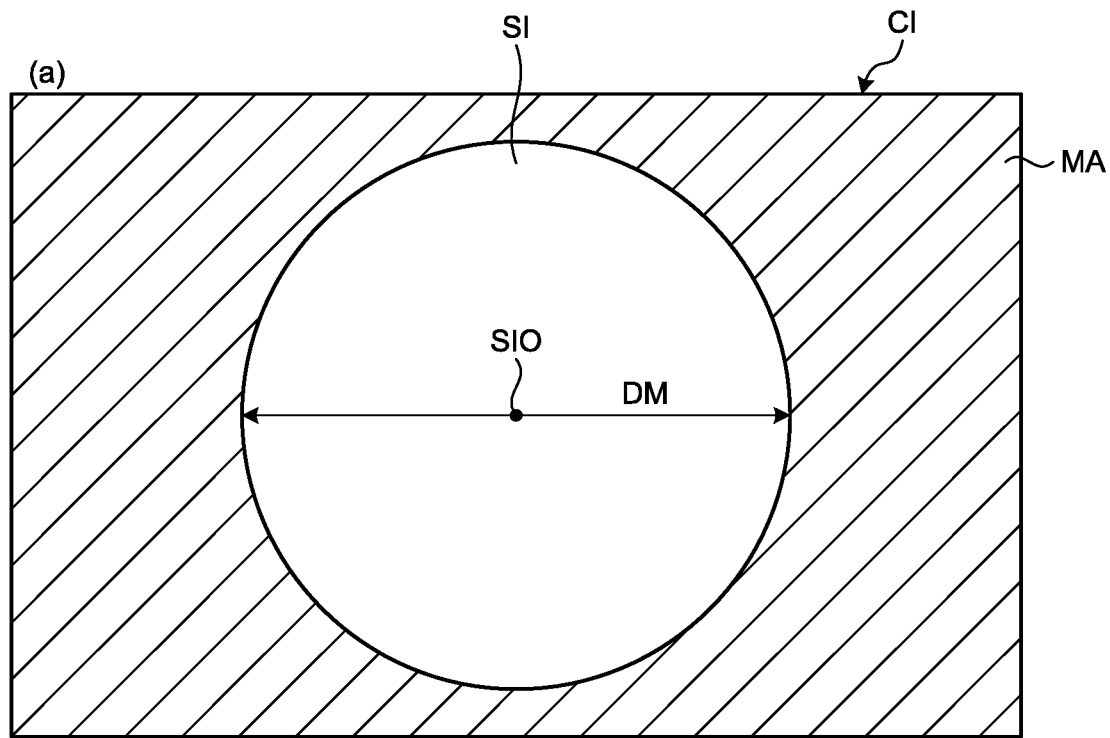
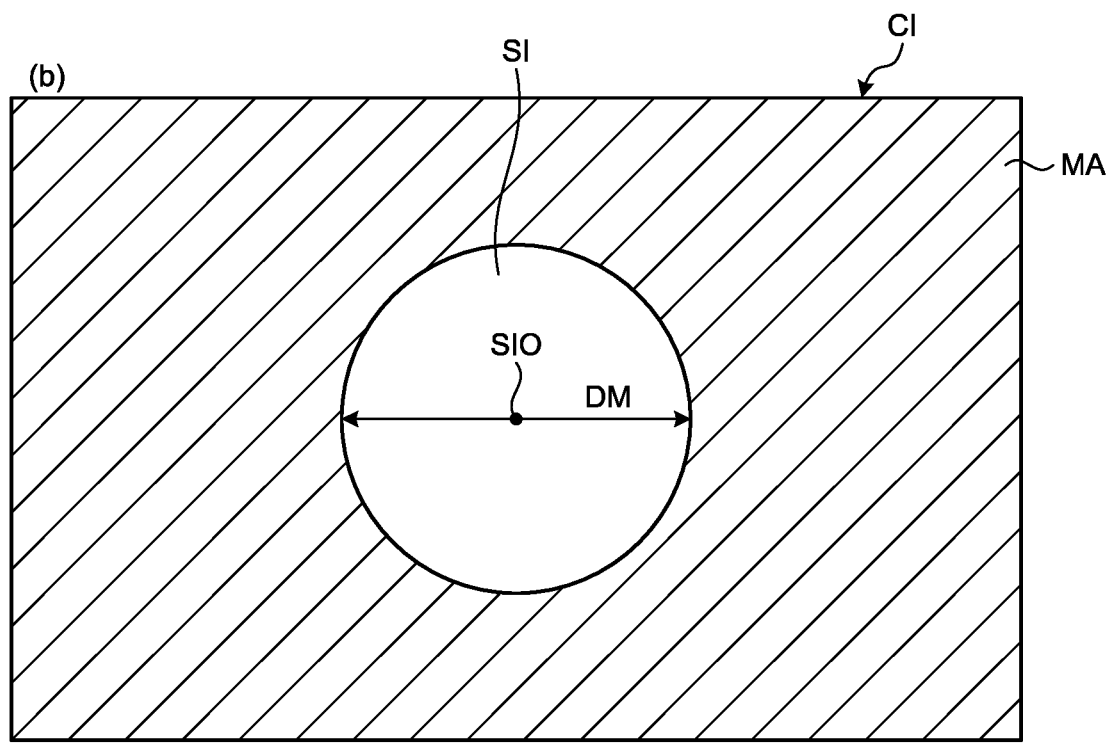

ENDOSCOPE SYSTEM AND CIRCUITRY THAT CORRECTS DISTORTION BASED ON IMAGE SIZE

CROSS-REFERENCE TO RELATED APPLICATION(S)

The present application claims priority to and incorporates by reference the entire contents of Japanese Patent Application No. 2017-157489 filed in Japan on Aug. 17, 2017.

BACKGROUND

The present disclosure relates to an endoscope system. In the past, an endoscope system has been known which enables observation of an interior of a subject such as a human being and a mechanical structure in medical and industrial fields, respectively (for example, refer to Japanese Laid-open Patent Publication No. 2015-134039 A).

The endoscope system (endoscope apparatus) described in the above publication includes an endoscope inserted into an interior of a subject to obtain a subject image of the subject from a distal end, a camera head detachably connected to an eyepiece unit of the endoscope to capture the subject image and generate a captured image, a control device that processes the captured image to generate a display image signal, and a display device that displays the image based on the display image signal.

SUMMARY

As an endoscope (rigid endoscope), there are a plurality of types of endoscopes having different types of internal optical systems (for example, different lens diameters) or the like. That is, a distortion amount (aberration amount) of an optical distortion (distortion aberration) caused by the internal optical system is different for each type of the endoscope. For this reason, in order to generate display image signal, it is necessary to provide a configuration for correcting the optical distortion of the captured image using a correction parameter suitable for the endoscope connected to the camera head. However, the conventional endoscope systems do not include such a configuration.

In this regard, it is demanded to provide a technology capable of improving convenience by correcting the optical distortion of the captured image using a correction parameter suitable for the endoscope whatever endoscope is connected to the camera head among a plurality of types of endoscopes.

The present disclosure has been made in view of the above, and is directed to an improvement to an endoscope system.

According to an aspect of the present disclosure, an endoscope system is provided which includes a camera head detachably connected to an eyepiece unit of a plurality of types of endoscopes inserted into a subject, the camera head including an imaging unit that captures a subject image received from an endoscope among the plurality of types of endoscopes that is connected to the eyepiece; a detection unit that detects a size of the subject image in a captured image obtained by the imaging unit, in accordance with a luminance signal of each pixel in the captured image; and a distortion correction processing unit that corrects an optical distortion of the captured image depending on the size of the subject image in the captured image, the size being detected by the detection unit.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a diagram illustrating a mask diameter detection process;

FIG. 4 is diagrams illustrating the mask diameter detection process;

DETAILED DESCRIPTION

Figure 1:
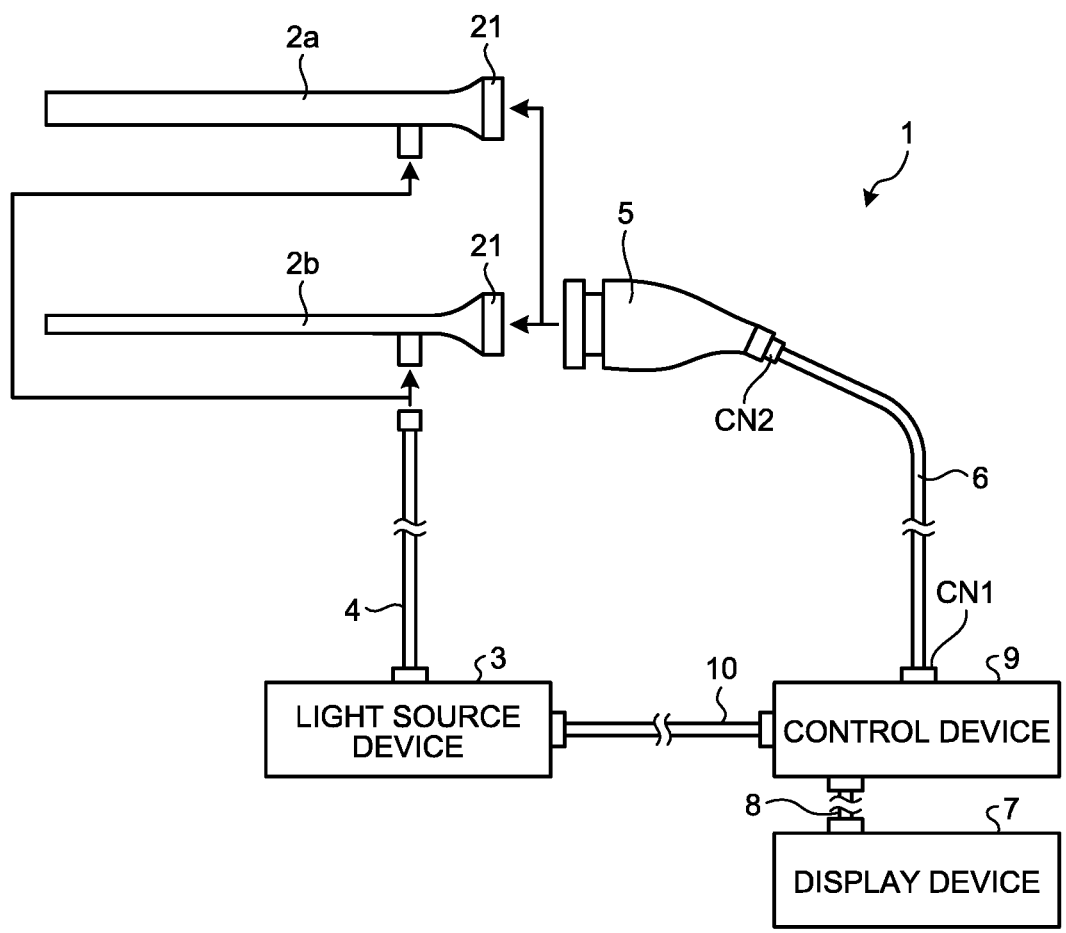
FIG. 1 is a diagram illustrating a schematic configuration of an endoscope system according to an embodiment of the disclosure.

Modes for embodying the present disclosure (hereinafter, referred to as "embodiments") will now be described with reference to the accompanying drawings. Note that the embodiments described below are not intended to limit the present disclosure. In the description of the drawings, like reference numerals denote like elements.

Schematic Configuration of Endoscope System FIG. 1 is a diagram illustrating a schematic configuration of an endoscope system according to an embodiment of the disclosure.

The endoscope system 1 is a system used for medical purposes to observe an interior of a living body. The endoscope system 1 includes a plurality of types of endoscopes (in this embodiment, two types of endoscopes including first and second endoscopes 2a and 2b), a light source device 3, a light guide 4, a camera head 5, a first transmission cable 6, a display device 7, a second transmission cable 8, a control device 9, and a third transmission cable 10.

Each of the first and second endoscopes 2a and 2b is a rigid endoscope. That is, each of the first and second endoscopes 2a and 2b is formed of a rigid or at least partially flexible material in an elongated shape and is inserted into a living body. Each of the first and second endoscopes 2a and 2b internally has an optical system having one or a plurality of lenses for condensing a subject image. Note that the first and second endoscopes 2a and 2b have different diameters. In this embodiment, the first endoscope 2a has a diameter larger than that of the second endoscope 2b. In addition, each of the first and second endoscopes 2a and 2b internally has an optical system having a size matching the diameter. In addition, the endoscope system 1 uses one of the first and second endoscopes 2a and 2b depending on an observation target inside a living body and the like.

The light source device 3, to which one end of the light guide 4 is connected, supplies light for illuminating the interior of the living body to the one end of the light guide 4 under control of the control device 9.

The light guide 4 has detachably connected at the one end to the light source device 3 and end detachably connected at the other to the first or second endoscope 2a or 2b. In addition, the light guide 4 transmits the light supplied from the light source device 3 from the one end to the other end to supply the light to the first or second endoscope 2a or 2b. The light supplied to the first or second endoscope 2a or 2b is emitted from a distal end of the first or second endoscope 2a or 2b and is irradiated onto the interior of the living body. Light (subject image) irradiated onto the interior of the living body and reflected therefrom is condensed by the optical system of the first or second endoscope 2a or 2b.

The camera head 5 is detachably connected to each eyepiece unit 21 of the first and second endoscopes 2a and 2b. In addition, the camera head 5 captures the subject image condensed by the first or second endoscope 2a or 2b under control of the control device 9 and outputs an image signal (raw signal) obtained through the imaging. This image signal is an image signal having a resolution of, for example, 4 K or higher.

Note that a specific configuration of the camera head 5 will be described in more details below.

The first transmission cable 6 has one end detachably connected to the control device 9 through a connector CN1 and the other end detachably connected to the camera head 5 through a connector CN2. In addition, the first transmission cable 6 transmits an image signal or the like output from the camera head 5 to the control device 9, and transmits each of a control signal, a synchronization signal, a clock, power, and the like output from the control device 9 to the camera head 5.

Note that the image signal or the like may be transmitted from the camera head 5 to the control device 9 through the first transmission cable 6 either as an optical signal or as an electric signal. Similarly, the control signal, the synchronization signal, and the clock may also be transmitted from the control device 9 to the camera head 5 through the first transmission cable 6 as an optical signal or as an electrical signal.

The display device 7 is a liquid crystal display (LCD) or an organic electroluminescence (EL) display and displays an image based on the image signal from the control device 9 under control of the control device 9.

The second transmission cable 8 has one end detachably connected to the display device 7 and the other end detachably connected to the control device 9. In addition, the second transmission cable 8 transmits the image signal processed by the control device 9 to the display device 7.

The control device 9 includes a central processing unit (CPU) or the like and comprehensively controls the operations of the light source device 3, the camera head 5, and the display device 7.

Note that a specific configuration of the control device 9 will be described below.

The third transmission cable 10 has one end detachably connected to the light source device 3 and the other end detachably connected to the control device 9. In addition, the third transmission cable 10 transmits the control signal from the control device 9 to the light source device 3.

Configuration of Camera Head

Next, a configuration of the camera head 5 will be described.

Figure 2:
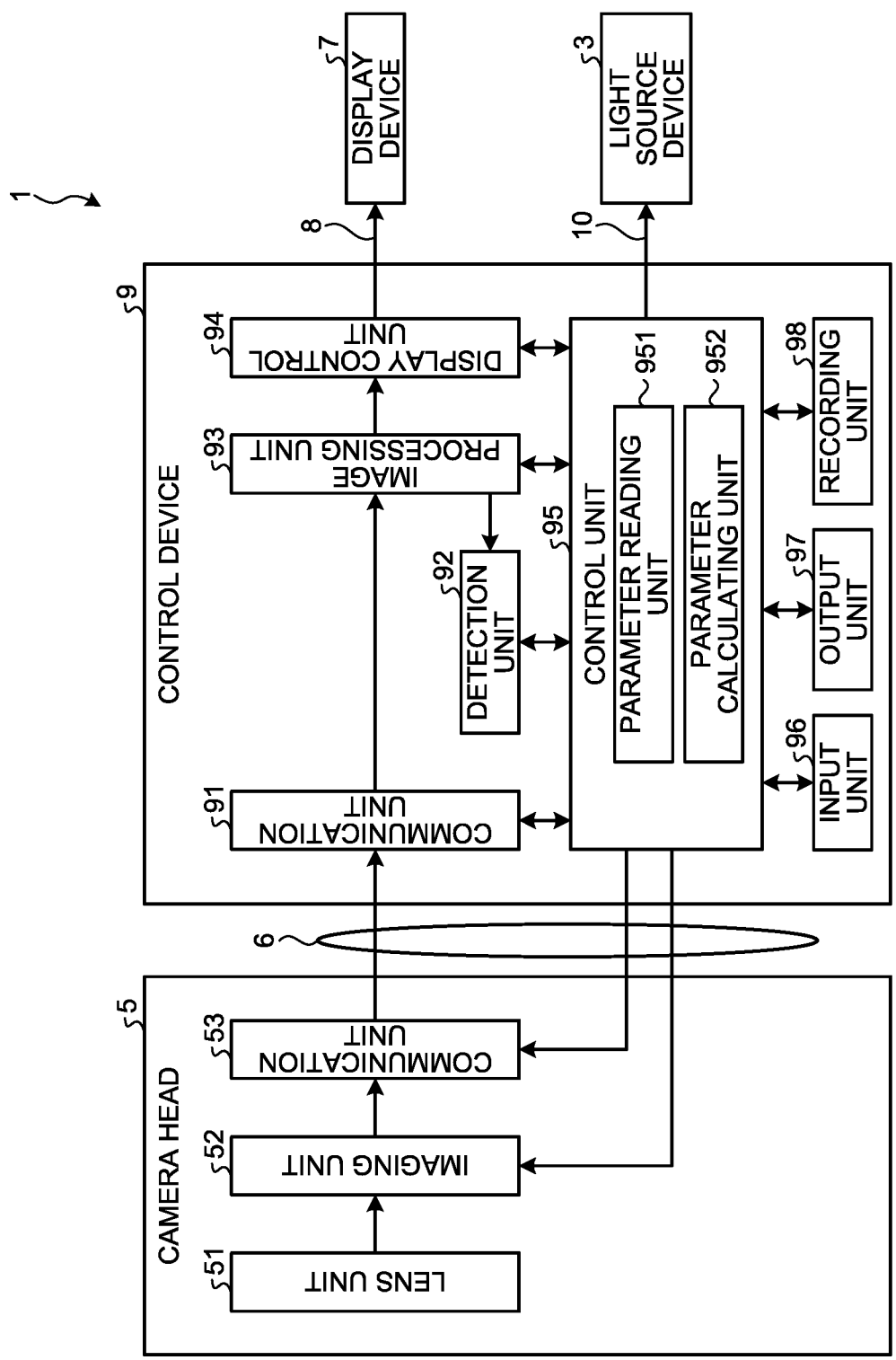
FIG. 2 is a block diagram illustrating configurations of a camera head and a control device.

FIG. 2 is a block diagram illustrating configurations of the camera head 5 and the control device 9.

Note that, for convenient description purposes, the connector CN1 between the first transmission cable 6 and the control device 9, the connector CN2 between the first transmission cable 6 and the camera head 5 are omitted in FIG. 2. Similarly, a connector between the second transmission cable 8 and the control device 9, a connector between the second transmission cable 8 and the display device 7, a connector between the third transmission cable 10 and the control device 9, and a connector between the third transmission cable 10 and the light source device 3 are omitted in FIG. 2.

The camera head 5 has a lens unit 51, an imaging unit 52, and a communication unit 53.

The lens unit 51 includes one or a plurality of lenses to focus the subject image collected by the first or second endoscope 2a or 2b on an imaging surface of the imaging unit 52.

The imaging unit 52 captures an image of an interior of a living body under control of the control device 9. Although not illustrated in details, the imaging unit 52 includes an image sensor, such as a charge-coupled device (CCD) or a complementary metal oxide semiconductor (CMOS), that receives the subject image focused by the lens unit 51 and converts it into an electric signal (analog signal), and a signal processing unit that performs signal processing for the electric signal (analog signal) from the image sensor and outputs an image signal (raw signal (digital signal)).

The communication unit 53 serves as a transmitter that transmits the image signal (raw signal (digital signal)) output from the imaging unit 52 to the control device 9 through the first transmission cable 6. The communication unit 53 has, for example, a high-speed serial interface for performing communication of the image signal with the control device 9 through the first transmission cable 6 at a transmission rate of 1 Gbps or higher, for example.

Configuration of Control Device

Next, a configuration of the control device 9 will be described with reference to FIG. 2.

The control device 9 includes a communication unit 91, a detection unit 92, an image processing unit 93, a display control unit 94, a control unit 95, an input unit 96, an output unit 97, and a recording unit 98.

The communication unit 91 serves as a receiver that receives the image signal (raw signal (digital signal)) output from the camera head 5 (communication unit 53) through the first transmission cable 6. The communication unit 91 has, for example, a high-speed serial interface for performing communication of the image signal with the communication unit 53 at a transmission rate of 1 Gbps or higher, for example.

FIGS. 3 and 4 are diagrams illustrating a mask diameter detection process. Specifically, a part (a) of FIG. 3 is a diagram illustrating an exemplary captured image CI captured by the imaging unit 52. A part (b) of FIG. 3 is a diagram illustrating a distribution of the luminance value on a horizontal line L5 of the captured image CI of the part (a) of FIG. 3. A part (a) of FIG. 4 is a diagram illustrating the captured image CI captured by the imaging unit 52 while the first endoscope 2a is connected to the camera head 5. The part (b) of FIG. 4 is a diagram illustrating the captured image CI captured by the imaging unit 52 while the second endoscope 2b is connected to the camera head 5.

Here, the light (subject image) reflected from an interior of a living body and collected by the first or second endoscope 2a or 2b has a substantially circular crosssectional shape. For this reason, a subject image SI in the captured image CI has a substantially circular shape as illustrated in the part (a) of FIG. 3 and the parts (a) and (b) of FIG. 4. That is, the captured image CI includes the subject image SI and a mask region MA other than the subject image SI (the black portion of the part (a) of FIG. 3 and the hatched portion of the parts (a) and (b) of FIG. 4). In addition, the size of the subject image SI is different depending on the diameters of the first and second endoscopes 2a and 2b. That is, the size of the subject image SI (the part (a) of FIG. 4) formed by connecting the first endoscope 2a to the camera head 5 is larger than the size of the subject image SI (the part (b) of FIG. 4) formed by connected the second endoscope 2b to the camera head 5.

The detection unit 92 executes a mask diameter detection process for detecting the size of the subject image SI in the captured image CI. In this embodiment, the detection unit 92 detects a diameter DM of the subject image SI (the part (a) of FIG. 3 and FIG. 4, hereinafter, referred to as a mask diameter DM) as a size of the subject image SI in the captured image CI.

Specifically, the detection unit 92 acquires a luminance signal (Y signal) out of the image signals (Y and $C_B/C_R$ signals) processed by the image processing unit 93. In addition, the detection unit 92 detects each distribution of the luminance value in horizontal lines L1 to L14 (the part (a) of FIG. 3) of a plurality of lines (fourteen lines in this embodiment) of the captured image CI on the basis of the luminance signal (Y signal). Here, in the captured image CI, the region of the subject image SI has a luminance value higher than that of the mask region MA. That is, for example, in the luminance distribution on the horizontal line L5, the luminance value increases between two boundary points BP of the subject image SI and the mask region MA, and decreases in other regions as illustrated in the part (b) of FIG. 3. With this, the detection unit 92 recognizes a plurality of boundary points BP between the subject image SI and the mask region MA by detecting luminance distributions on the horizontal lines L1 to L14. In addition, the detection unit 92 detects a center position SIO of the subject image SI in the captured image CI by calculating a curvature center of the plurality of boundary points BP. Furthermore, the detection unit 92 detects a mask diameter DM by calculating a distance (number of pixels) between the center position SIO and any one of the boundary points BP. In the following description, the mask diameter DM detected through the mask diameter detection process will be referred to as a "detection mask diameter DM" for convenient description purposes.

The image processing unit 93 processes the image signal (raw signal (digital signal)) output from the camera head 5 (communication unit 53) and received by the communication unit 91 under control of the control unit 95.

For example, the image processing unit 93 performs raw processing, such as an optical black subtraction process, and a demosaic process for the image signal (raw signal (digital signal)) to convert the raw signal (image signal) to an RGB signal (image signal). In addition, the image processing unit 93 performs RGB processing, such as a white balance adjustment process, gamma correction, and Y-C conversion (conversion from an RGB signal to a luminance signal and a color difference signal (Y, $C_B/C_R$ signals) for the RGB signal (image signal). Furthermore, the image processing unit 93 executes Y-C processing, such as color difference correction and noise reduction for the Y and $C_B/C_R$ signals (image signals).

The image processing unit 93 executes a distortion correction process for the Y and $C_B/C_R$ signals (image signals), subsequent to the Y-C processing.

Figure 5:
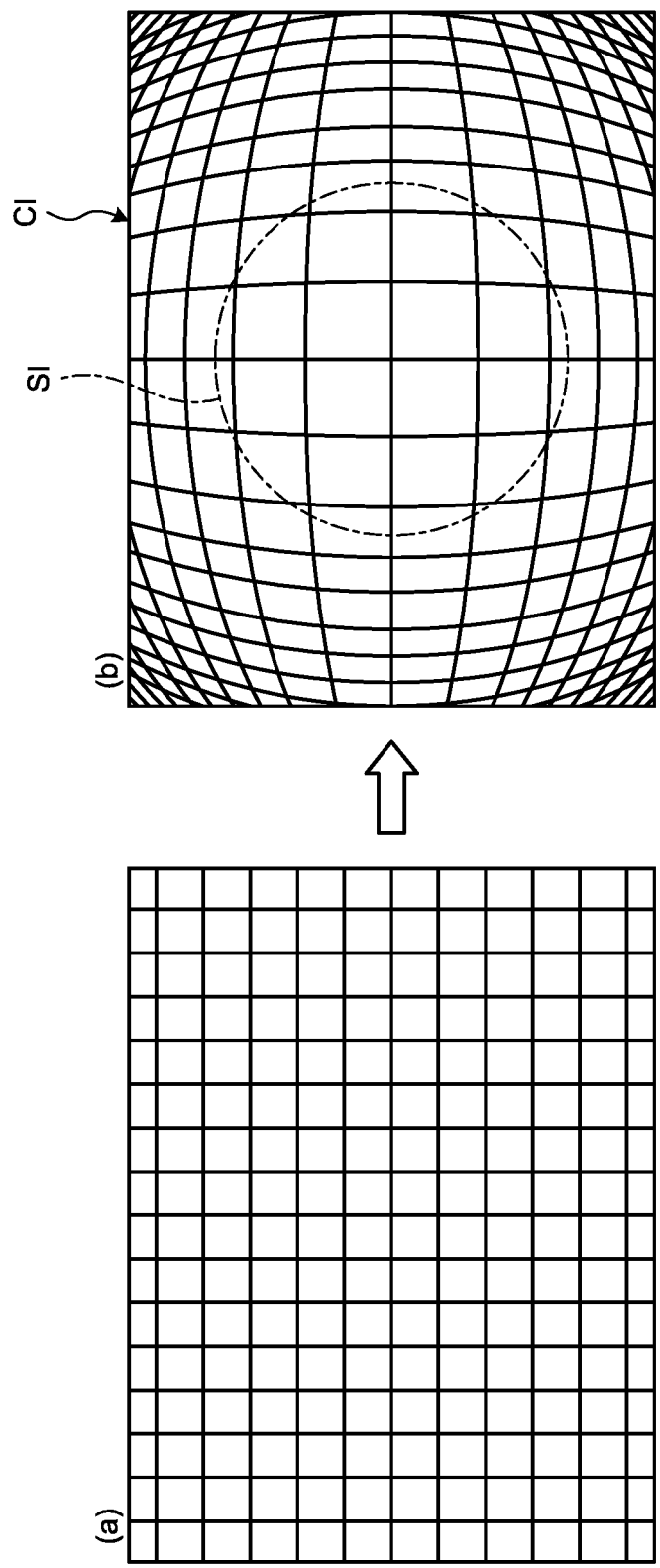
FIG. 5 is a diagram illustrating a distortion correction process.
Figure 6:
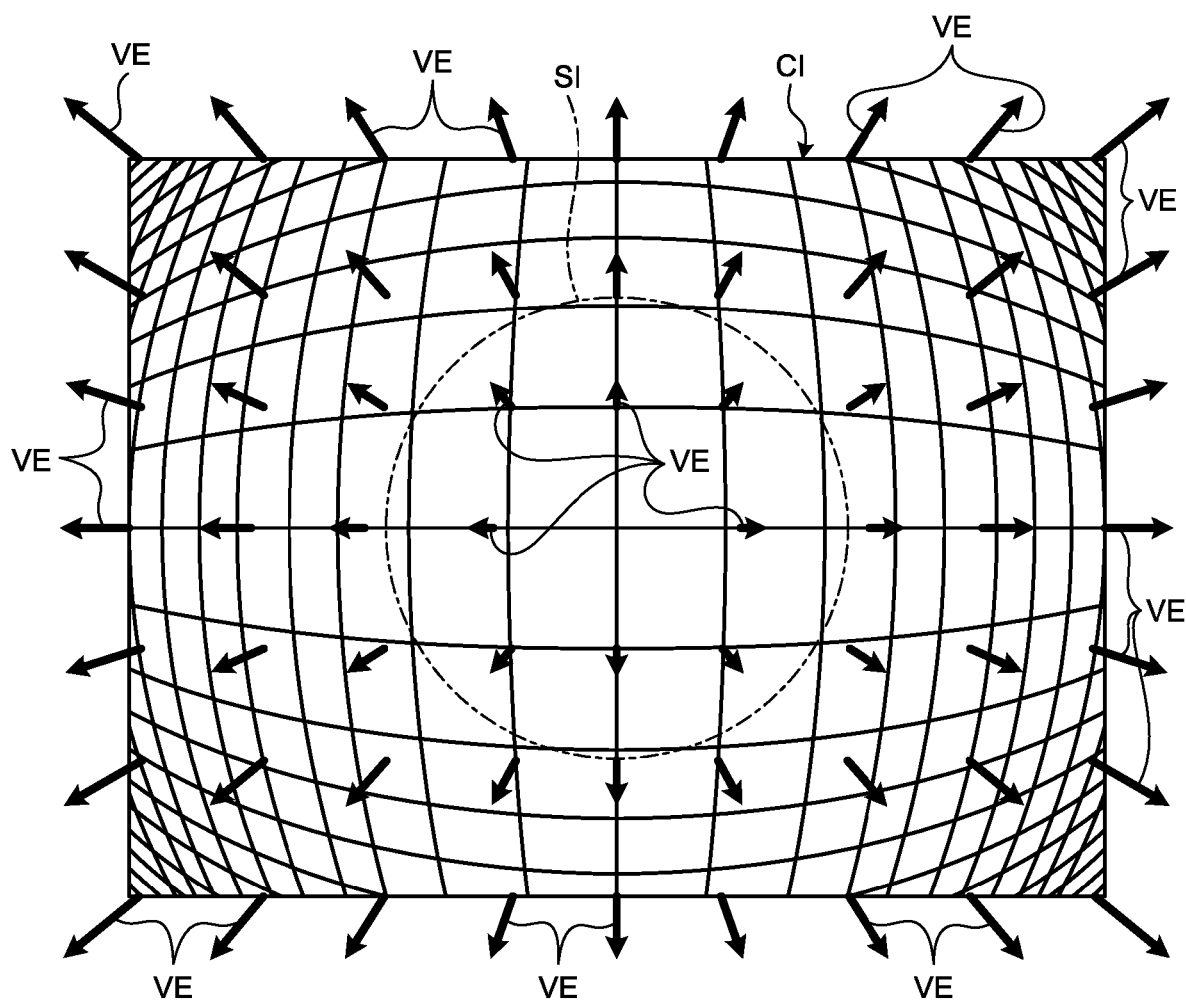
FIG. 6 is a diagram illustrating the distortion correction process.

FIGS. 5 to 6 are diagrams illustrating a distortion correction process. Specifically, a part (a) of FIG. 5 is a diagram illustrating a grid-like subject having horizontal and vertical lines perpendicular to each other. A part (b) of FIG. 5 is a diagram illustrating the captured image CI obtained by capturing an image of the subject in the part (a) of FIG. 5. Note that, in the part (b) of FIG. 5, a barrel distortion aberration is generated by the optical system provided in the first or second endoscope 2a or 2b. FIG. 6 is a diagram illustrating an exemplary correction parameter (an existing correction parameter and a new correction parameter) for correcting the distortion aberration for the captured image CI having the generated barrel distortion aberration of the part (b) of FIG. 5.

Here, when a barrel distortion aberration is generated by the optical system provided in the first or second endoscope 2a or 2b, horizontal and vertical straight lines originally perpendicular to each other in the subject of the captured image CI (the part (a) of FIG. 5) are distorted like a barrel spherically swelled outward from the lens center (the part (b) of FIG. 5). In addition, the image processing unit 93 executes a distortion correction process using the correction parameter (an existing correction parameter or a new correction parameter) output from the control unit 95 to correct the optical distortion (distortion aberration) of the captured image CI.

Specifically, the correction parameter (an existing correction parameter or a new correction parameter) includes a plurality of correction vectors VE provided in a plurality of predetermined positions (coordinate values) inside the captured image CI as illustrated in FIG. 6. These correction vectors VE are directed outward from the lens center (a center position of the captured image CI), and their magnitudes increase as a distance from the lens center increases. In addition, in the distortion correction process, the image processing unit 93 moves pixels to a plurality of predetermined positions of the captured image CI according to the direction and the magnitude of the correction vector VE. In addition, regarding to each of other positions, namely, positions other than the predetermined positions, the image processing unit 93 calculates the correction vector from the correction vectors VE at, for example, four predetermined positions close to each of other position. Then, the image processing unit 93 moves the pixels to these positions outward according to the directions and the magnitudes of the calculated correction vectors.

The image processing unit 93 executes a magnification process for the Y and $C_B/C_R$ signals (image signals), subsequent to the Y-C processing.

Figure 7:
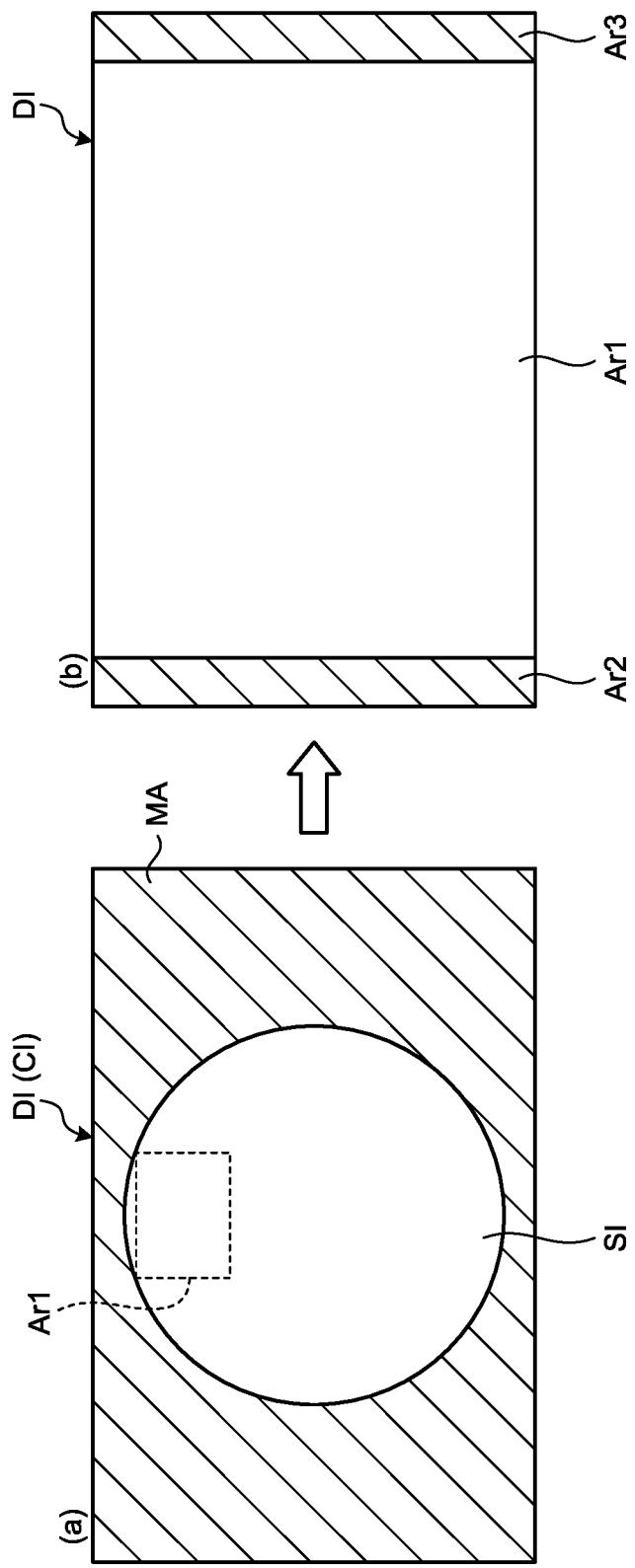
FIG. 7 is a diagram illustrating a magnification process.

FIG. 7 is a diagram illustrating the magnification process. Specifically, a part (a) of FIG. 7 illustrates a display image DI (captured image CI) displayed on the display device 7 before executing the magnification process. A part (b) of FIG. 7 illustrates a display image DI displayed on the display device 7 after executing the magnification process.

The image processing unit 93 executes the magnification process in response to a user manipulation for magnifying a part of the regions of the subject image SI (for example, the region Ar1 in the part (a) of FIG. 7).

Specifically, the image processing unit 93 cuts out a region Ar1 selected by a user from the captured image CI in the magnification process. In addition, the image processing unit 93 adds black level regions Ar2 and Ar3 (the part (b) of FIG. 7) in both left and right sides of the region Ar1 to form an image having the same aspect ratio as that of the screen of the display device 4. In addition, this image is displayed on the display device 4 as a display image DI.

The image processing unit 93 corresponds to a distortion correction processing unit and a magnification processing unit according to the present disclosure.

The display control unit 94 creates a display image signal on the basis of the image signal, subsequent to the processing of the image processing unit 93 (such as the raw processing, the RGB processing, the Y-C processing, the distortion correction process, and the magnification process) under control of the control unit 95. Then, the display control unit 94 outputs the image signal to the display device 7 through the second transmission cable 8.

The control unit 95 has, for example, a central processing unit (CPU) or the like and outputs a control signal through the first to third transmission cables 6, 8, and 10 to control the operations of the light source device 3, the camera head 5, and the display device 7 and control all of the operations of the control device 9. As illustrated in FIG. 2, the control unit 95 has a parameter reading unit 951 and a parameter calculating unit 952.

The parameter reading unit 951 determines whether or not an existing correction parameter associated with the same mask diameter DM as the detection mask diameter DM detected by the detection unit 92 is recorded in the recording unit 98. Then, when it is determined that an existing correction parameter associated with the same mask diameter DM as the detection mask diameter DM is recorded in the recording unit 98, the parameter reading unit 951 reads the existing correction parameter from the recording unit 98 and outputs it to the image processing unit 93.

If the parameter reading unit 951 determines that the existing correction parameter associated with the same mask diameter DM as the detection mask diameter DM is not recorded in the recording unit 98, the parameter calculating unit 952 reads at least one of "N" existing correction parameters (where "N" denotes any integer equal to greater than "2") recorded in the recording unit 98. Then, the parameter calculating unit 952 calculates a new correction parameter matching the detection mask diameter DM using at least one of the existing correction parameters and outputs the new correction parameter to the image processing unit 93.

The input unit 96 has a manipulation device such as a mouse, a keyboard, and a touch panel to accept a user manipulation from a user such as a doctor (for example, a user manipulation for enlargedly displaying a part of the regions (for example, the region Ar1 of the part (a) of FIG. 7) of the subject image SI). In addition, the input unit 96 outputs a manipulation signal depending on a user manipulation to the control unit 95. That is, the input unit 96 has a function as a manipulation accepting unit according to the present disclosure.

The output unit 97 has a loudspeaker, a printer, or the like to output various types of information.

The recording unit 98 records a program executed by the control unit 95, information necessary in processing performed by the image processing unit 93 or the control unit 95, and the like (such as the existing correction parameters described above).

Here, the aberration amount of the distortion aberration is different depending on the optical system. That is, the aberration amount of the distortion aberration caused by the optical system of the first endoscope 2a is different from the aberration amount of the distortion aberration caused by the optical system of the second endoscope 2b. In addition, there is a relationship between the aberration amount of the distortion aberration and the size of the subject image SI (mask diameter DM). In this embodiment, the recording unit 98 records "N" existing correction parameters respectively associated with different "N" mask diameters DM (the first to (N)th mask diameters DM1 to DMN). Each of the "N" existing correction parameters includes a plurality of correction vectors VE calculated in advance from the aberration amount matching the mask diameter DM. In addition, the "N" existing correction parameters include a plurality of existing correction parameters matching other mask diameters DM in addition to the existing correction parameter matching the mask diameter DM of the first endoscope 2a and the existing correction parameter matching the mask diameter DM of the second endoscope 2b.

Operations of Endoscope System

Next, operations of the aforementioned endoscope system 1 will be described.

Figure 8:
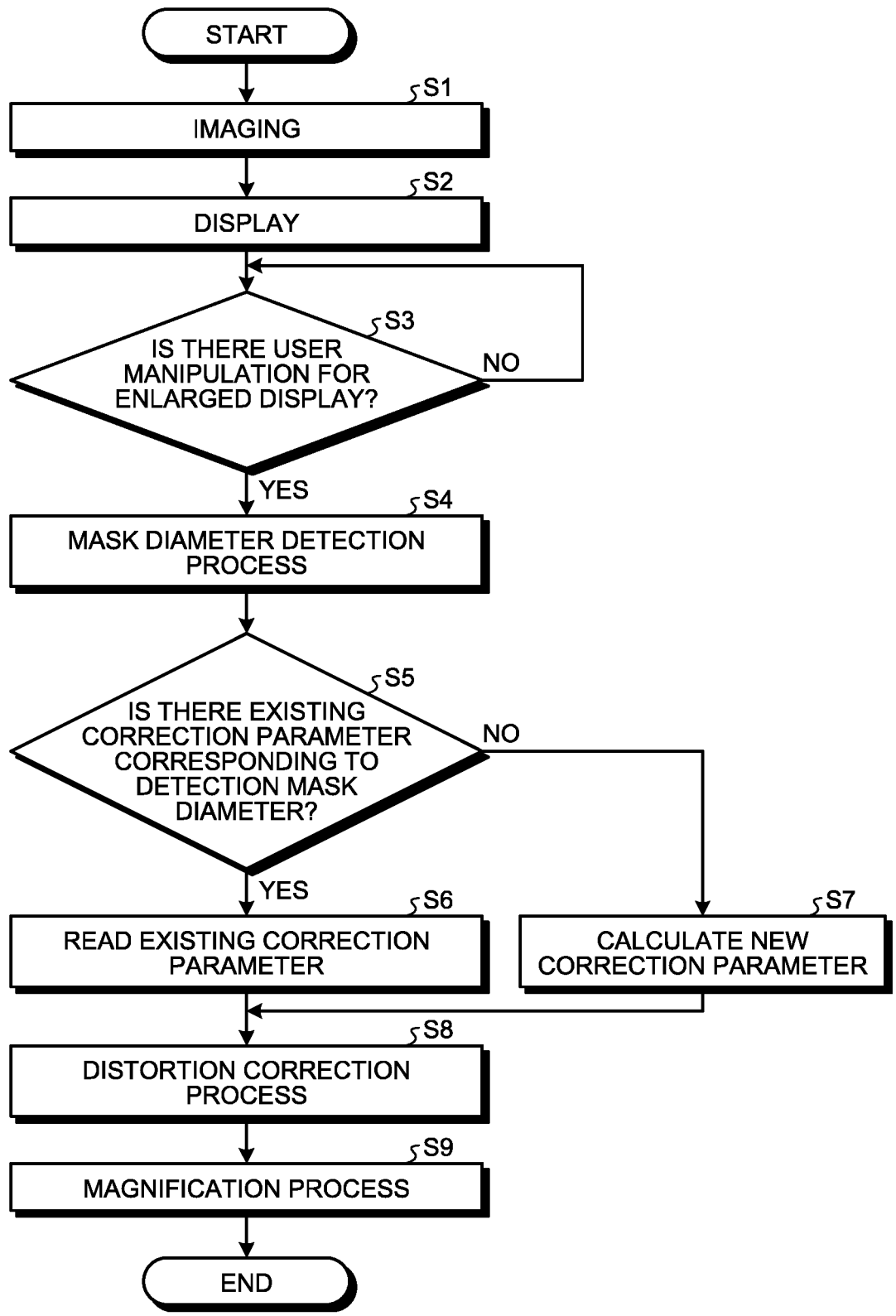
FIG. 8 is a flowchart illustrating operations of the endoscope system.

FIG. 8 is a flowchart illustrating operations of the endoscope system 1.

First, the control device 9 controls operations of the camera head 5 and the display device 7 to start imaging of the subject image SI collected by the endoscope (such as the first or second endoscope 2a or 2b) connected to the camera head 5 (step S1), and to display the captured image CI obtained through this imaging on the display device 7 (step S2).

After step S2, the control unit 95 monitors, at all times, whether or not there is a user manipulation on the input unit 96 for enlargedly displaying a part of the regions of the subject image SI (for example, the region Ar1 of the part (a) of FIG. 7) from a user such as a doctor (step S3).

If it is determined that there is a user manipulation (step S3: Yes), the detection unit 92 executes the mask diameter detection process (step S4).

After step S4, the parameter reading unit 951 determines whether or not an existing correction parameter associated with the same mask diameter DM as the detection mask diameter DM detected in the mask diameter detection process of step S4 is recorded in the recording unit 98 (step S5).

If it is determined that the existing correction parameter associated with the same mask diameter DM as the detection mask diameter DM is recorded (step S5: Yes), the parameter reading unit 951 reads the existing correction parameter from the recording unit 98 and outputs it to the image processing unit 93 (step S6).

Meanwhile, when it is determined that the existing correction parameter associated with the same mask diameter DM as the detection mask diameter DM is not recorded (step S5: No), the parameter calculating unit 952 calculates a new correction parameter, for example, as described below and outputs it to the image processing unit 93 (step S7).

Here, it is assumed that, regarding the "N" first to (N)th mask diameters DM1 to DMN respectively associated with the "N" existing correction parameters recorded in the recording unit 98, the first mask diameter DM1 has the smallest size, and the size increases in order of the ordinal number. In addition, it is assumed that the detection mask diameter DM has a size between the third mask diameter DM3 and the fourth mask diameter DM4.

The parameter calculating unit 952 reads two existing correction parameters respectively associated with two mask diameters DM close to the detection mask diameter DM (in the aforementioned case, the third diameter DM3 and the fourth mask diameter DM4) around the detection mask diameter DM among the "N" existing correction parameters recorded in the recording unit 98. Then, the parameter calculating unit 952 calculates a new correction parameter matching the detection mask diameter DM by interpolating (for example, linear interpolation) the two read existing correction parameters.

After step S6 or S7, the image processing unit 93 executes a distortion correction process only for the region instructed in step S3 in the captured image CI (for example, the region Ar1 of the part (a) of FIG. 7) using the correction parameter (the existing correction parameter or the new correction parameter) output from the control unit 95 (step S8). In addition, the image processing unit 93 executes a magnification process after the distortion correction process (step S9).

According to this embodiment described above, the following effects can be achieved.

The endoscope system 1 according to this embodiment employs the following configuration by focusing on a relationship between the aberration amount of the distortion aberration caused by the optical system provided in the endoscope (for example, first and second endoscopes 2a and 2b) and the mask diameter DM.

In the endoscope system 1, a plurality of existing correction parameters for correcting the optical distortion of the captured image CI are respectively associated with a plurality of different mask diameters DM and are recorded in advance. In addition, in the endoscope system 1, the mask diameter DM of the captured image CI is detected on the basis of the luminance signal of each pixel of the captured image CI. Furthermore, in the endoscope system 1, the optical distortion of the captured image CI is corrected using the existing correction parameter associated with the same mask diameter DM as the detection mask diameter DM among the plurality of existing correction parameters recorded in advance.

Therefore, in the endoscope system 1 according to this embodiment, it is possible to improve convenience by correcting an optical distortion of the captured image CI using a correction parameter for the endoscope whatever endoscope is connected to the camera head 5 among a plurality of types of endoscopes (for example, the first and second endoscopes 2a and 2b).

In the endoscope system 1 according to this embodiment, when the existing correction parameter associated with the same mask diameter DM as the detection mask diameter DM is not recorded, a new correction parameter matching the detection mask diameter DM is calculated using the plurality of existing correction parameters recorded in advance. In addition, in the endoscope system 1, an optical distortion of the captured image CI is corrected using the new correction parameter.

Therefore, even when a newly developed endoscope or an endoscope of any other company is connected to the camera head 5, it is possible to correct an optical distortion of the captured image CI using a correction parameter for the endoscope.

In the endoscope system 1 according to this embodiment, a distortion correction process is executed only for a part of the regions in the captured image CI (for example, the region Ar1 of the part (a) of FIG. 7) that is instructed to be enlargedly displayed.

Therefore, compared to a case where the distortion correction process is executed for the entire captured image CI, it is possible to reduce a processing load of the image processing unit 93.

Other Embodiments

While embodiments of the present disclosure have been described hereinbefore, it should be appreciated that the disclosure is not limited by the aforementioned embodiments.

Figure 9:
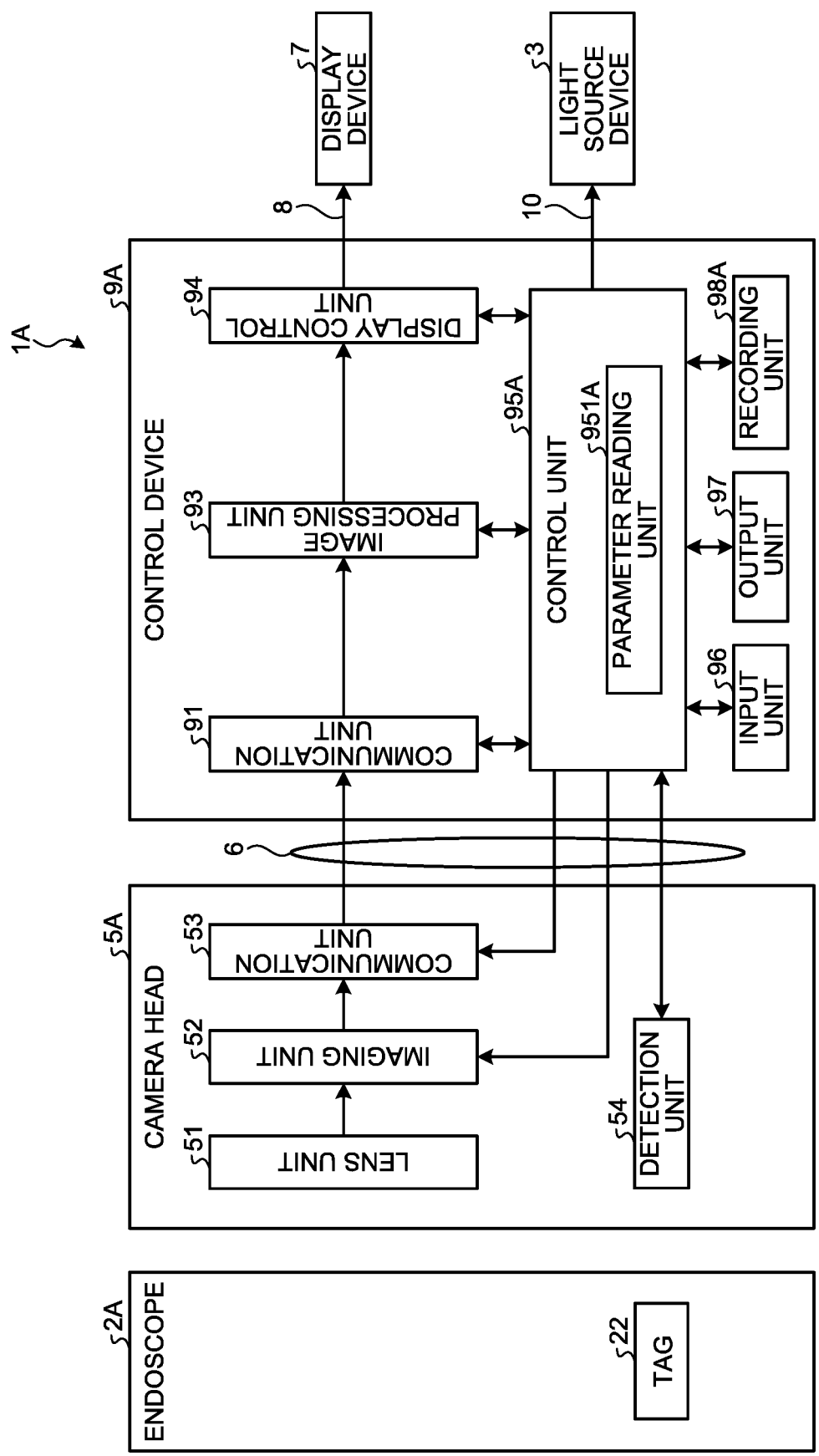
FIG. 9 is a diagram illustrating a first modification of the embodiment.

FIG. 9 is a diagram illustrating a first modification of the embodiment.

In the endoscope system 1 according to the aforementioned embodiment, the control device 9 (control unit 95) detects the detection mask diameter DM through the mask diameter detection process and reads the existing correction parameter associated with the same mask diameter DM as the detection mask diameter DM from the recording unit 98. However, the present disclosure is not limited thereto. For example, according to the first modification, an endoscope system 1A may be configured as illustrated in FIG. 9. That is, in the endoscope system 1A, a control device 9A (control unit 95A) acquires identification information of an endoscope 2A from the endoscope 2A connected to a camera head 5A and reads an existing correction parameter associated with the same identification information as the acquired identification information from a recording unit 98A.

Specifically, in the endoscope 2A, a tag 22 is added, as illustrated in FIG. 9, while such a tag is absent in the first and second endoscopes 2a and 2b described in the aforementioned embodiment.

The tag 22 includes, for example, a radio frequency identification (RFID) tag or the like and is provided in the eyepiece unit 21 and the like. In addition, the tag 22 records identification information unique to the endoscope 2A.

In the camera head 5A, as illustrated in FIG. 9, a detection unit 54 is added which is absent in the camera head 5 described in the aforementioned embodiment.

The detection unit 54 includes, for example, an RFID detection circuit or the like, and acquires the identification information recorded in the tag 22 under control of the control device 9A (control unit 95A). In addition, the detection unit 54 outputs the acquired identification information to the control unit 95A through the first transmission cable 6.

As understood by comparing FIG. 2 and FIG. 9, the detection unit 92 that exists in the control device 9 in the aforementioned embodiment is absent in the control device 9A. Moreover, a control unit 95A and a recording unit 98A are employed instead of the control unit 95 and the recording unit 98.

In the recording unit 98A, the information associated with the "N" recorded existing correction parameters is different from that of the recording unit 98 described in the aforementioned embodiment. Specifically, the "N" existing correction parameters recorded in the recording unit 98A are associated with identification information of the "N" different endoscopes, respectively. Each of the "N" existing correction parameters includes the plurality of correction vectors VE calculated in advance from the aberration amount of the distortion aberration caused by each optical system provided in each of the "N" endoscopes.

Compared to the control unit 95 described in the aforementioned embodiment, the parameter calculating unit 952 is absent in the control unit 95A as illustrated in FIG. 9. In addition, a parameter reading unit 951A is employed instead of the parameter reading unit 951.

The parameter reading unit 951A outputs a control signal to the detection unit 54 through the first transmission cable 6 and acquires the identification information recorded in the tag 22 of the endoscope 2A. In addition, the parameter reading unit 951A reads the existing correction parameter associated with the same identification information as the acquired identification information from the "N" existing correction parameters recorded in the recording unit 98A and outputs it to the image processing unit 93.

Note that, in the first modification described above, when the existing correction parameter associated with the same identification information as the identification information acquired from the endoscope 2A is not recorded in the recording unit 98A, similar to the aforementioned embodiment, a new correction parameter may be calculated.

Specifically, similar to the aforementioned embodiment, the "N" existing correction parameters recorded in the recording unit 98A are associated with the mask diameter DM in addition to the identification information. In addition, the detection unit 92 described in the aforementioned embodiment is added to the control device 9A. Furthermore, the parameter calculating unit 952 described in the aforementioned embodiment is added to the control unit 95A. Moreover, similar to the first embodiment described above, when the existing correction parameter associated with the same identification information as the identification information acquired from the endoscope 2 is not recorded in the recording unit 98A, the parameter calculating unit 952 calculates a new correction parameter matching the detection mask diameter DM using at least one of the "N" existing correction parameters and outputs the new correction parameter to the image processing unit 93.

Note that, in the first modification described above, identification information unique to the endoscope 2A is recorded in the tag 22. However, without limiting thereto, a correction parameter itself used in the distortion correction process may also be recorded. That is, the parameter reading unit 951A acquires the correction parameter recorded in the tag 22 through the detection unit 54 and outputs the correction parameter to the image processing unit 93.

Figure 10:
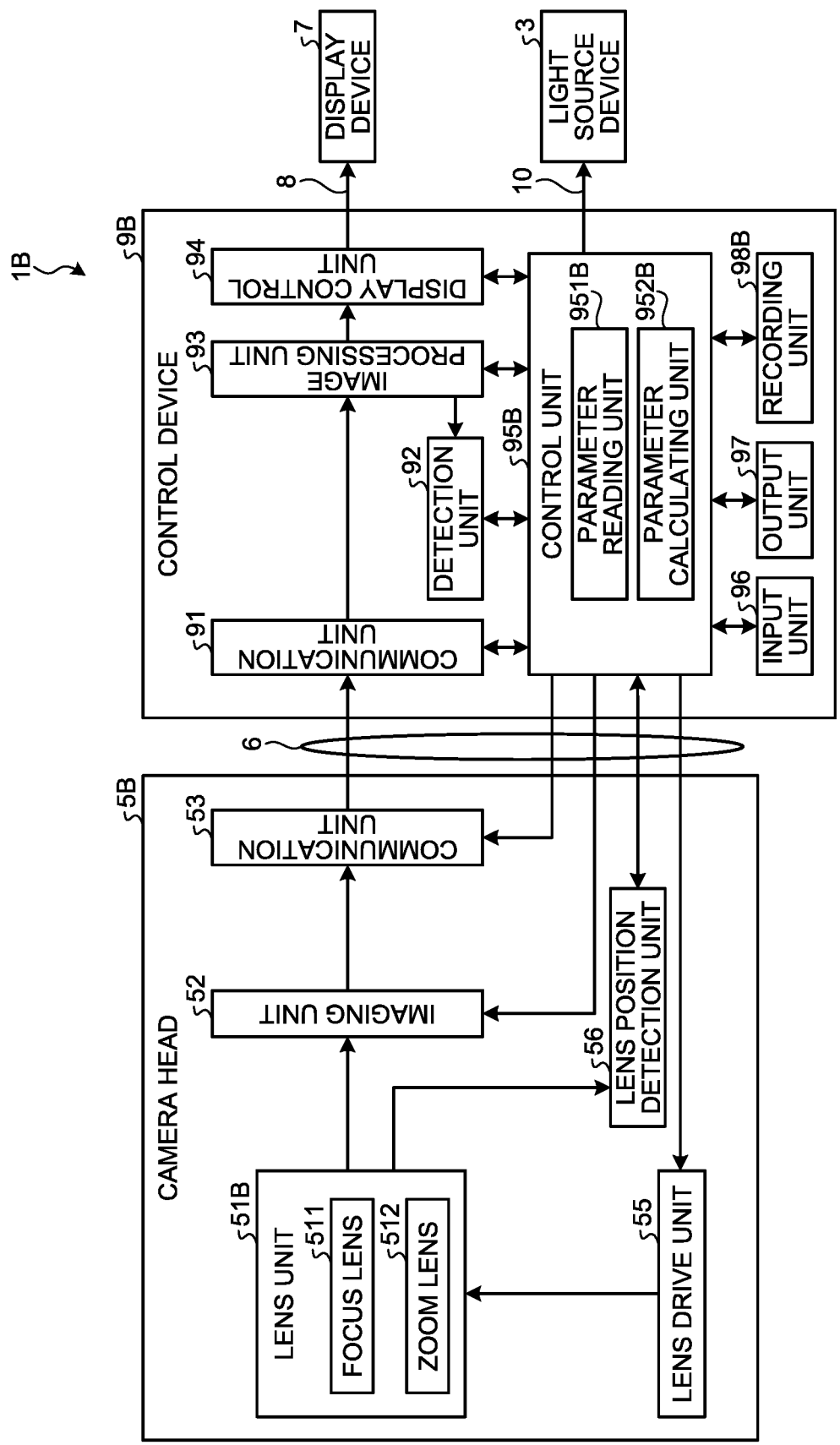
FIG. 10 is a diagram illustrating a second modification of the embodiment.
Figure 11:
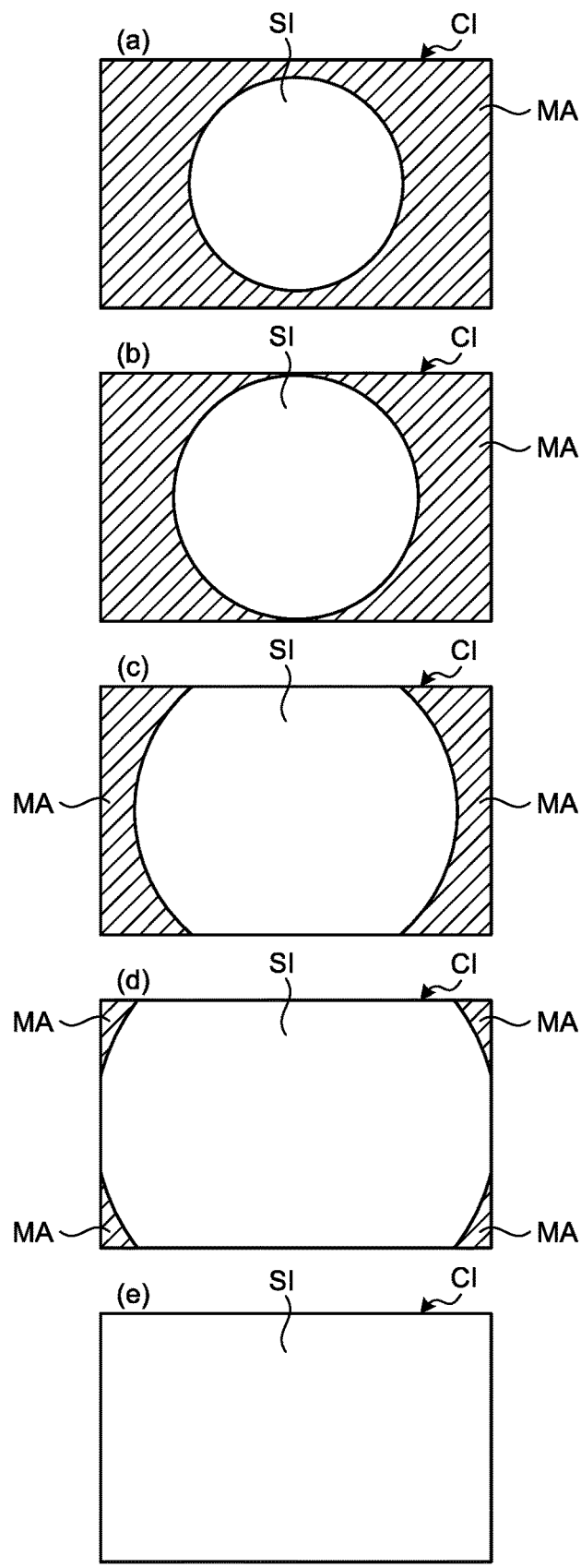
FIG. 11 is diagrams illustrating the second modification of the embodiment.

FIG. 10 and FIG. 11 are diagrams illustrating a second modification of the embodiment.

The endoscope system 1 according to the aforementioned embodiment may be modified to adjust a focal point or an angle of view as in an endoscope system 1B according to the second modification of FIG. 10.

Specifically, compared to the camera head 5 described in the aforementioned embodiment, a lens unit 51B instead of the lens unit 51 is employed in a camera head 5B of the endoscope system 1B as illustrated in FIG. 10. In addition, camera head 5B is provided with a lens drive unit 55 and a lens position detection unit 56.

The lens unit 51B includes a plurality of lenses movable along an optical axis and focuses a subject image SI collected by the first or second endoscope 2a or 2b on an imaging plane of the imaging unit 52. The lens unit 51B has a focus lens 511 and a zoom lens 512 as illustrated in FIG. 10.

The focus lens 511 includes one or a plurality of lenses and adjusts a focal point by moving along the optical axis.

The zoom lens 512 includes one or a plurality of lenses and adjusts an angle of view by moving along the optical axis.

The lens unit 51B is provided with a focus mechanism (not illustrated) for moving the focus lens 511 along the optical axis or an optical zoom mechanism (not illustrated) for moving the zoom lens 512 along the optical axis.

The lens drive unit 55 operates the focus mechanism or the optical zoom mechanism described above under control of a control device 9B to adjust a focal point or an angle of view of the lens unit 51B.

The lens position detection unit 56 includes a photo interrupter and a position sensor, and detects a lens position of the focus lens 511 (hereinafter, referred to as a focus position) or a lens position of the zoom lens 512 (hereinafter, referred to as a zoom position). In addition, the lens position detection unit 56 outputs a detection signal matching the focus position and the zoom position to the control device 9B through the first transmission cable 6.

Compared to the control device 9 described in the aforementioned embodiment, a control unit 95B and a recording unit 98B instead of the control unit 95 and the recording unit 98 are employed in the control device 9B of the endoscope system 1B as illustrated in FIG. 10.

Here, as a zoom position is changed, the size of the subject image SI is also changed as illustrated in parts (a) to (e) of FIG. 11. Note that the parts (a) to (e) of FIG. 11 schematically illustrate captured images CI when the zoom ratio is sequentially increased by changing the zoom position. That is, when the zoom position is changed, for example, while a distortion correction process is executed using a new correction parameter or an existing correction parameter matching the detection mask diameter DM of the subject image SI captured at a reference zoom position, this existing correction parameter or new correction parameter is not an appropriate correction parameter. Therefore, it is difficult to adequately correct an optical distortion of the captured image CI after the zoom ratio is changed. For this reason, it is necessary to change the existing correction parameter or the new correction parameter depending on the zoom position. Note that it is also necessary to change the existing correction parameter or the new correction parameter even when the focus position is changed.

Compared to the recording unit 98 described in the aforementioned embodiment, the recording unit 98B has different information associated with the "N" recorded existing correction parameters. Specifically, assuming that the focus position, the zoom position, and the mask diameter DM are used as a set of associating information, the "N" existing correction parameters recorded in the recording unit 98B are respectively associated with a plurality of different sets of associating information.

Compared to the control unit 95 described in the aforementioned embodiment, a parameter reading unit 951B and a parameter calculating unit 952B instead of the parameter reading unit 951 and the parameter calculating unit 952 are employed in the control unit 95B as illustrated in FIG. 10.

The parameter reading unit 951B recognizes the current focus position and the current zoom position depending on the detection signal from the lens position detection unit 56. In addition, the parameter reading unit 951B recognizes the current detection mask diameter DM detected by the detection unit 92 through the mask diameter detection process. Then, the parameter reading unit 951B determines whether or not the recording unit 98B records an existing correction parameter associated with the same associating information as the current focus position, the current zoom position, and the detection mask diameter DM. When the existing correction parameter associated with the same associating information as the current focus position, the current zoom position, and the detection mask diameter DM is determined to be recorded in the recording unit 98B, the parameter reading unit 951B reads the existing correction parameter from the recording unit 98B, and outputs it to the image processing unit 93.

If the parameter reading unit 951B determines that the existing correction parameter associated with the same associating information as the current focus position, the current zoom position, and the detection mask diameter DM is not recorded in the recording unit 98B, the parameter calculating unit 952B executes the following processing.

That is, the parameter calculating unit 952B reads at least two existing correction parameters respectively associated with at least two pieces of associating information close to the current focus position, the current zoom position, and the detection mask diameter DM from the "N" existing correction parameters recorded in the recording unit 98B. In addition, the parameter calculating unit 952B calculates a new correction parameter matching the current focus position, the current zoom position, and the current detection mask diameter DM using the at least two existing correction parameters, and outputs the new correction parameter to the image processing unit 93.

Note that, in the second modification described above, similar to the aforementioned embodiment, the "N" existing correction parameters recorded in the recording unit 98B may also be respectively associated with only "N" different mask diameters DM. Here, each of the "N" mask diameters DM corresponds to each of the mask diameters DM of the subject image SI when an image is captured at the reference zoom position. In addition, when the aforementioned information is recorded in the recording unit 98B, the parameter reading unit 951B and the parameter calculating unit 952B serve as first and second functions, respectively, described below.

The first function is as follows.

The parameter reading unit 951B recognizes the current focus position and the current zoom position depending on the detection signal from the lens position detection unit 56. In addition, the parameter reading unit 951B recognizes the current detection mask diameter DM detected by the detection unit 92 through the mask diameter detection process. In addition, the parameter reading unit 951B estimates the mask diameter DM of the subject image SI obtained by capturing an image at the reference zoom position on the basis of the current focus position, the current zoom position, and the current detection mask diameter DM. Hereinafter, for convenient description purposes, the estimated mask diameter DM will be referred to as an "estimated mask diameter DM". Furthermore, the parameter reading unit 951B determines whether or not the existing correction parameter associated with the same mask diameter DM as the estimated mask diameter DM is recorded in the recording unit 98B. When the existing correction parameter associated with the same mask diameter DM as the estimated mask diameter DM is determined to be recorded in the recording unit 98B, the parameter reading unit 951B reads this existing correction parameter from the recording unit 98B, and outputs it to the parameter calculating unit 952B.

If the parameter reading unit 951B determines that the existing correction parameter associated with the same mask diameter DM as the estimated mask diameter DM is recorded in the recording unit 98B, the parameter calculating unit 952B executes the following processing.

That is, the parameter calculating unit 952B adjusts the existing correction parameter output from the parameter reading unit 951B depending on the current focus position and the current zoom position, and outputs the adjusted existing correction parameter to the image processing unit 93.

Meanwhile, when the parameter reading unit 951B determines that the existing correction parameter associated with the same mask diameter DM as the estimated mask diameter DM is not recorded in the recording unit 98B, the parameter calculating unit 952B executes the following processing.

That is, the parameter calculating unit 952B reads at least two existing correction parameters respectively associated with at least two mask diameters DM close to the estimated mask diameter DM from the "N" existing correction parameters recorded in the recording unit 98B. In addition, the parameter calculating unit 952B calculates a new correction parameter matching the estimated mask diameter DM using the at least two existing correction parameters. Furthermore, the parameter calculating unit 952B adjusts the new correction parameter depending on the current focus position and the current zoom position, and outputs the adjusted new correction parameter to the image processing unit 93.

The second function is as follows.

The parameter reading unit 951B outputs a control signal to the lens drive unit 55 through the first transmission cable 6 to change the zoom position to the reference zoom position. In addition, the parameter reading unit 951B executes the mask diameter detection process in the detection unit 92 to recognize the detection mask diameter DM detected in the mask diameter detection process (the mask diameter DM of the captured image CI captured at the reference zoom position). In addition, the parameter reading unit 951B determines whether or not the existing correction parameter associated with the same mask diameter DM as the detection mask diameter DM is recorded in the recording unit 98B. Furthermore, when it is determined that the existing correction parameter associated with the same mask diameter DM as the detection mask diameter DM is recorded in the recording unit 98B, the parameter reading unit 951B reads the existing correction parameter from the recording unit 98B, and outputs it to the parameter calculating unit 952B. Moreover, the parameter reading unit 951B outputs a control signal to the lens drive unit 55 through the first transmission cable 6 to change the zoom position to the original zoom position before the zoom position was changed to the reference zoom position.

If the parameter reading unit 951B determines that the existing correction parameter associated with the same mask diameter DM as the detection mask diameter DM is recorded in the recording unit 98B, the parameter calculating unit 952B executes the following processing.

That is, the parameter calculating unit 952B adjusts the existing correction parameter output from the parameter reading unit 951B depending on the current focus position and the current zoom position (the original zoom position before changing the zoom position to the reference zoom position), and outputs the adjusted existing correction parameter to the image processing unit 93.

Meanwhile, when the parameter reading unit 951B determines that the existing correction parameter associated with the same mask diameter DM as the detection mask diameter DM is not recorded in the recording unit 98B, the parameter calculating unit 952B executes the following processing.

That is, the parameter calculating unit 952B reads at least two existing correction parameters respectively associated with at least two mask diameters DM close to the detection mask diameter DM from the "N" existing correction parameters recorded in the recording unit 98B. In addition, the parameter calculating unit 952B calculates a new correction parameter matching the detection mask diameter DM using at least the two existing correction parameters. In addition, the parameter calculating unit 952B adjusts the new correction parameter depending on the current focus position and the current zoom position (the original zoom position before changing the zoom position to the reference zoom position), and outputs the adjusted new correction parameter to the image processing unit 93.

Note that, when the zoom ratio is equal to or higher than a predetermined value in the second modification described above, or when the detection mask diameter DM is equal to or larger than a predetermined size, the distortion correction process may not be executed. For example, in the state of a part of FIG. 11, the zoom ratio is equal to or higher than a predetermined value, or the detection mask diameter DM is equal to or larger than a predetermined size. Therefore, detection accuracy of the detection mask diameter DM is degraded. For this reason, in this case, the distortion correction process is not executed.

In the embodiment and the first and second modifications described above, the detection unit 92 detects the mask diameter DM as a size of the subject image SI according to the present disclosure. However, without limiting thereto, the area of the subject image SI or the mask region MA may also be detected.

In the embodiment and the first and second modifications described above, the processing of steps S4 to S8 may be executed before step S3. That is, in step S8, the distortion correction process may be executed for the entire captured image CI instead of the region instructed in step S3 (for example, the region Ar1 of the part (a) of FIG. 7).

In the embodiment and the first and second modifications described above, a manipulation accepting unit according to the present disclosure that receives a user manipulation for enlargedly displaying a part of the subject image SI may also be provided, for example, in the camera heads 5, 5A, and 5B without limiting to the control devices 9, 9A, and 9B (input unit 96).

In the embodiment and the first and second modifications described above, a part of the configurations of the camera heads 5, 5A, and 5B or a part of the configurations of the control devices 9, 9A, and 9B may also be provided, for example, in the connector CN1 or CN2.

In the embodiment and the first and second modifications described above, the endoscope systems 1, 1A, and 1B may also be an endoscope system used in the industrial fields to observe a subject such as a mechanical structure.

Incidentally, there is a relationship between the distortion amount (aberration amount) of an optical distortion (distortion aberration) caused by an optical system provided in the endoscope and the size of the subject image in the captured image. The present disclosure has been made by focusing on this relationship.

Specifically, in the endoscope system according to the present disclosure, a plurality of existing correction parameters for correcting an optical distortion of the captured image respectively associated with the sizes of a plurality of different subject images are recorded in advance. In addition, in the endoscope system, the size of the subject image in the captured image is detected on the basis of the luminance signal of each pixel in the captured image. Furthermore, in the endoscope system, the optical distortion of the captured image is corrected using the existing correction parameter associated with the same size of the subject image as the size of the detected subject image among a plurality of existing correction parameters recorded in advance.

Therefore, using the endoscope system according to the present disclosure, it is possible to improve convenience by correcting an optical distortion of the captured image using a correction parameter suitable for the endoscope whatever endoscope is connected to the camera head among a plurality of types of endoscopes.

Although the present disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope system comprising:
   a camera head detachably connected to an eyepiece of a plurality types of endoscopes to be inserted into a subject, the plurality of types of endoscopes outputting a plurality of images having different sizes, respectively, the camera head including a camera that captures a subject image received from an endoscope among the plurality of types of endoscopes that is connected to the eyepiece; and
   circuitry configured to:
   detect a size of the subject image in a captured image obtained by the camera, in accordance with a luminance signal of each pixel in the captured image; and
   correct an optical distortion of the captured image depending on the size of the subject image from among sizes of the plurality of the images that are different from one another.

2. The endoscope system according to claim 1, further comprising:
   a memory that stores a plurality of existing correction parameters respectively associated with the sizes of the plurality of images that are different from one another to correct an optical distortion of the captured image; and
   the circuitry configured to
   select an existing correction parameter associated with a same size of the subject image as the size of the subject image detected among the plurality of existing correction parameters stored in the memory, and
   correct an optical distortion of the captured image using the existing correction parameter selected.

3. The endoscope system according to claim 1, wherein the circuitry is configured to:
   accept a user manipulation for enlargedly displaying a part of the subject image;
   cut out the part of the subject image from the captured image in response to the user manipulation; and
   correct an optical distortion in only the part of the subject image in response to the user manipulation.

4. The endoscope system according to claim 2, wherein the circuitry is configured to
   determine whether or not the existing correction parameter associated with the same size of the subject image as the size of the subject image detected is stored in the memory,
   calculate a new correction parameter matching the size of the subject image using at least one of the plurality of existing correction parameters when the existing correction parameter associated with the same size of the subject image detected is not stored in the memory, and
   correct an optical distortion of the captured image using the new correction parameter.

5. The endoscope system according to claim 4, wherein the circuitry is configured to
   calculate the new correction parameter by interpolating two existing correction parameters respectively associated with two images each having a size close to the size of the subject image detected among the plurality of existing correction parameters.

6. Circuitry for use with an endoscope system including a camera head detachably connected to an eyepiece of a plurality of types of endoscopes to be inserted into a subject, the camera head including a camera that captures a subject image received from an endoscope among the plurality of types of endoscopes that is connected to the eyepiece, the plurality of types of endoscopes outputting a plurality of images having different sizes, respectively, the circuitry being configured to:

detect a size of the subject image in a captured image obtained by the camera, in accordance with a luminance signal of each pixel in the captured image; and correct an optical distortion of the captured image depending on the same size of a subject image from among sizes of the plurality of the images that are different from one another.

7. The circuitry according to claim 6, wherein the circuitry is configured to:

read a plurality of existing correction parameters respectively associated with sizes of a plurality of images that are different from one another to correct an optical distortion of the captured image from a memory;

select an existing correction parameter associated with a same size of the subject image as the size of the subject image detected among the plurality of existing correction parameters; and correct an optical distortion of the captured image using the existing correction parameter selected.

8. The circuitry according to claim 7, wherein the circuitry s configured to determine whether or not the existing correction parameter associated with the same size of the subject image as the size of the subject image detected is stored in the memory;

calculate a new correction parameter matching the size of the subject image using at least one of the plurality of existing correction parameters when the existing correction parameter associated with the same size of the subject image detected is not stored in the memory; and correct an optical distortion of the captured image using the new correction parameter.

9. The circuitry according to claim 8, wherein the circuitry is configured to calculate the new correction parameter by interpolating two existing correction parameters respectively associated with two images each having a size close to the size of the subject image detected among the plurality of existing correction parameters.

10. The circuitry according to claim 6, wherein the circuitry is configured to:

accept a user manipulation for enlargedly displaying a part of the subject image;

cut out the part of the subject image from the captured image in response to the user manipulation; and correct an optical distortion in only the part of the subject image in response to the user manipulation.

* * * * *